United States Patent [19]

Tesch

[11] Patent Number: 4,530,869
[45] Date of Patent: Jul. 23, 1985

[54] HEAT PACK AND PROCESS FOR THE PREPARATION OF A HEAT PACK

[76] Inventor: Gunter H. Tesch, 22, Rte. de la Heitera, Fribourg, Switzerland, CH-1700

[21] Appl. No.: 526,816

[22] Filed: Aug. 26, 1983

[30] Foreign Application Priority Data

Sep. 9, 1982 [CH] Switzerland .......................... 5356/82

[51] Int. Cl.³ .......................... B32B 5/06; B32B 31/18
[52] U.S. Cl. .......................... 428/69; 28/107; 156/250; 428/74; 428/75; 428/174; 428/219; 428/284; 428/300; 428/484
[58] Field of Search .......................... 428/69, 75, 76, 300, 428/192, 194, 484, 284, 174, 219; 156/250; 128/402, 403, 1 R; 424/29, 38; 28/107

[56] References Cited

U.S. PATENT DOCUMENTS

| | | | |
|---|---|---|---|
| 3,122,142 | 2/1964 | Crowe | 604/369 |
| 3,900,651 | 8/1975 | Hoppe et al. | 428/218 |
| 4,205,113 | 5/1980 | Hermansson et al. | 428/300 |
| 4,409,271 | 10/1983 | Pehr | 428/69 |

Primary Examiner—Paul J. Thibodeau
Attorney, Agent, or Firm—Bacon & Thomas

[57] ABSTRACT

A heat pack and a process for its preparation are described wherein the heat pack comprises an earth-like mass between two outer layers surrounding the mass and the two outer layers are joined together by means of holding fibers uniformly distributed over their entire surface area. The joining of the three layers may be effected by a needle bonding process known in the needle tufting process of the textile industry. Webs of the three-layer system needle bonded in this manner are cut into pieces according to their application, thereby forming the heat packs as such, and packaged into foil bags in which the heat packs may be stored and heated.

33 Claims, 4 Drawing Figures

HEAT PACK AND PROCESS FOR THE PREPARATION OF A HEAT PACK

The invention concerns a heat pack comprising two outer layers enclosing an inner earth-like mass and which outer layers are joined together, at least at the borders, and a process for its preparation.

This general type of heat pack is described in DE-OS No. 2 301 821. In this known heat pack, an earth-like mass is placed between two layers surrounding the mass. The earth-like mass therein consists of a watery mud paste. One of the layers, which is at least liquid permeable, consists of a net-like, wide mesh fabric, which because of its permeability assures the direct contact of the layer of mud paste with the part of the body to be treated. For application, the known heat pack is placed directly onto the part of the body to be treated with the net-like fabric in contact with the body. The second layer surrounding the mass consists of a metal foil, supported by a plastic sheet which is impermeable to water and is on the side facing away from the layer of mud paste.

In this known heat pack, a series of further layers is provided. Thus, a heat insulating layer is placed on the aforementioned plastic sheet, which may consist of, for example, a moltoprene foam layer and which is covered by a further plastic sheet. The two plastic sheets which are impermeable to water are welded together in the area of their borders, so that the foam layer is enclosed in a water tight manner. On the side opposite to this system of layers, there is a cover sheet which may be lifted or removed and is located on the net-like fabric. The cover sheet is covered further by a protective sheet. All of the sheets and the net-like fabric are joined together at the circumferential border of the heat pack. The joint of the protective sheet with the other sheets, especially the above-mentioned outer plastic sheet, is releasable and resealable on three edges of the pack. This known heat pack may be heated in hot water. In the course of the first application of the pack, the protective sheet is released at the aforementioned three edges and folded away, whereupon the cover sheet covering the fabric is separated along tearaway lines and possibly removed entirely from the pack. The pack is then placed with the net-like fabric on the part of the body to be treated and the mud paste is caused by the contact pressure to slightly penetrate through the mesh of the fabric, thereby coming into direct contact with the skin of the part of the body to be treated. Following the application, the heat pack is resealed by means of the protective sheet, for which purpose compression locking means are provided on the said three borders.

The configuration and application of this known heat pack is relatively complicated; in particular, the application of the known heat pack is restricted to heat treatment with an aqueous mud paste. A further disadvantage of the known heat pack consists of the fact that if pressure is applied to part of its area, the mud paste is displaced from this location and accumulates in the adjacent areas. It is therefore very difficult to control the thickness of the layer of the mud paste.

In the case of a heat pack wherein essentially only mud paste is provided, the transfer of heat varies over the time of application, as the mud is slowly cooled.

Certain melting masses are also known, which may be used for thermal treatments and which are mixed in part with an earth-like mass, such as a mud or fango. The known mud-paraffin or fango-paraffin packs can be used only professionally by masseurs and/or physicians. The known packs are heated in a heating oven until they are free-flowing. The liquid is placed onto a sheet, for example, of a plastic material and solidifies slowly beginning at the outer side of the molten mass, while the inside of the pack remains liquid. The pack, solidified on the outside is placed immediately and carefully onto the patient. In the course of the application of the pack to the patient the inside of the pack solidifies slowly. The pack remains, during the entire solidification period, within a certain temperature range and releases the heat of solidification. As long as this known pack is not completely solidified, no pressure may be applied to it as, otherwise, the outer, already solidified layer of the otherwise homogeneous pack will burst and the liquid released.

With these known paraffin packs, it is again not possible to maintain a certain or constant layer thickness accurately over the entire surface of the pack.

Certain paraffin packs are further known, in which the paraffin is sealed in a gas and liquid tight plastic sheet, whereby only the release of heat from the pack may be utilized. If pressure is applied to this pack, the thickness of the layer varies and the release of heat becomes nonuniform.

It is therefore an object of the invention to provide a heat pack of this type that is simple in its application, insures a uniform release of heat over the entire application and the thickness of which does not vary even under pressure affecting only parts thereof.

This object is attained from a heat pack comprising two outer layers enclosing an inner layer of an earth-like mass and a melting mass, and wherein the layers are connected to each other by means of holding fibers distributed over their area. According to the invention, in a heat pack of this type, a layer of an earth-like mass and a melting mass is present between the two covering outer layers and these three layers are connected with each other by means of holding fibers distributed over their entire surface. In this manner, a heat pack is provided wherein the holding fibers prevent the shifting of the earth-like mass and the melting mass in the plane of the layer, first because they present an obstacle to the movements of the two masses, and, second, because the thickness of the layer cannot be increased, as the two outer layers are connected with each other by the holding fibers. According to a preferred embodiment, the three layers are needle bonded together, with the needle bonding being performed by means of a conventional needle fleecing machine.

The earth-like mass may comprise mud, fango, clay, particularly in the form of medicinal mud or the like. However, fillers, such as talcum powder, chalk, steatite or sand powder are also included herein. While these latter substances have no appreciable healing effect, they serve as supplemental heat reservoirs and as thickeners for the melting mass. They may be present in dry form.

For the melting mass, particularly, synthetic or natural hydrocarbon waxes are appropriate. Pure paraffins or mixtures of paraffins may be used; their melting points differing only slightly from each other.

The inner layer located between the two outer layers comprises 30–70% by weight of an earth-like mass and 70–30% by weight of the melting mass, with a preferred mixing ratio of 1:1. If the earth-like mass serves only as a further heat carrier and thickener, its proportion in the inner layer may be much less than the paraffin proportion, for example, even under 10%. In this regard, the earth-like mass may also contain active ingredients in liquid form or in the form of powders, such as oils, sulfur, vegetable extracts, or healing herbs or the like. In addition, the melting mass may contain means to prevent bleeding and to adjust the viscosity, in particular, thickeners. The inner layer comprising the earth-like mass and the melting mass is located between the two outer layers with a weight by unit area of 3–30 kg per m$^2$, preferably 8–15 kg per m$^2$.

In particular, when the three layers are needle bonded to each other, at least one outer layer comprises an actively needle bondable fiber fleece, having for example a weight per unit area of 20–350 g/m$^2$, preferably 100–180 g/m$^2$. In a preferred embodiment, this fiber fleece is preneedled and reinforced with a wide mesh filament netting or fabric.

According to a further embodiment, the other outer layer may also consist of a fiber fleece which has, for example, a weight per unit area of 100–200 g/m$^2$, but the second outer layer may also consist of a sheet preferably with a weight per unit area of 50–200 g/m$^2$. This sheet may be aluminum foil but is in particular a two-layer sheeting, one side whereof consists of a synthetic material and the other of aluminum. In place of foil, the second outer layer may consist of a fleece material, a woven fabric, or a fiber composite.

According to a particular embodiment, this foil is a so-called stepped foil, i.e., it contains small cup or pot like depressions.

In these cup-like depressions, the concentration of the melting mass may be larger with respect to the earth-like mass than in the rest of the inner layer.

The earth-like mass and the melting mass may be present in different forms between the two outer layers.

According to one particular embodiment of the invention, a mixture of the earth-like mass and the melting mass is present, which is prepared by stirring the dried and comminuted earth-like mass into a melt of the melting mass, thereby effecting an intimate mixture of the two masses. In the finished heat pack, there is therefore an inner layer present, which essentially represents a fully continuous layer, penetrated only by the holding fibers. The result is a highly homogeneous inner layer. The earth-like mass is thus embedded in the melting mass.

According to a further form of embodiment, both the earth-like mass and the melting mass is present in granular form. The dried, earth-like mass is, for example, first ground, while the melting mass may consist of granulated, cast, rasped particles or the like, with the particles preferably having irregular configurations with a minimum width of less than 1 mm and a greatest length in a range of 5–10 m.

However, in the inner layer, the melting mass may also be present as a homogeneous layer, while the earth-like mass is arranged in a dry and granular form between a water permeable outer layer and the melting mass. This embodiment has the advantage that during application, active ingredients may penetrate from the granular, earth-like mass through the outer layer to the body of the patient. The additionally provided layer of the melting mass provides only heat, which must penetrate the earth-like mass prior to acting on the body of the patient.

It follows from the foregoing that the inner layer of the earth-like mass and the melting mass may be structured differently, depending on the purpose of the inner layer and the type of treatment which is to be administered to the patient. It is conceivable to effect a separation of the layers in a heat pack in which both the earth-like mass and the melting mass are present in a granular form, so that on one side of the heat pack, the proportion of the earth-like mass is greater than on the other side of the inner layer. Such a nonuniform distribution is advisable especially when one of the two outer layers consists of a sheet of a synthetic plastic material, wherein in the vicinity of the plastic sheet, the melting mass is preferably present in a higher or exclusive concentration. This takes into consideration the fact that the melting mass serves essentially only as a heat reservoir and heat release material, while the earth-like masses are to release, in addition to heat, certain active ingredients which may be contained therein to the parts of the body to be treated.

It should be noted further that in particular by the needle bonding of the layer body and the formation of the holding fibers, the two outer layers are drawn to each other so that pressure is applied to the inner layer. To facilitate the application of the heat pack comprising the two outer layers and the inner layer, the pack is arranged between two gas and liquid tight sheets, with said sheets being sealingly joined together at their borders. These two sheets, joined together at their borders, represent not only a transport wrapping but also permit a dry, i.e., anhydrous, application of the pack. The packaged heat pack may be heated in a water bath, without the heat pack itself being wetted. For this purpose, the heat pack is placed together with the packaging for a longer period of time into boiling water, until the entire melting mass is melted. Depending on the thickness of the melting mass in the heat pack, this period of time is variable, although 15 minutes is generally considered to be adequate. If the two sheets are equipped (at least over part of their borders) with compression locking means, the heat pack may be repackaged following the opening of the closure and application.

Particularly for transportation and for the storage for extensive periods of time of a new, unused healing pack, it is advantageous to provide a vacuum within the packaging containing the heat pack. Even when a used heat pack is replaced between the sheets forming a packaging bag, the air should be removed as completely as possible from the bag, for which purpose in the case of the heat pack according to the invention, pointed or linear pressures may be applied without displacing the mass in the heat pack between the surrounding sheets. Such pressuring is not possible with the aforedescribed known heat packs, so that significant quantities of air remains in the known used packages, even when they are closed with a protective sheet. This results in slow spoiling of the earth-like mass of the prior art.

According to another particular embodiment, the circumferential borders of the heat pack formed by the two outer layers and the mixed layer are thinner than the rest of the heat pack, whereby within the area of these borders the melting mass penetrates the outer layers to a particularly great extent. This results not only in a more pleasing appearance of the heat pack, but the borders of the pack are quasi-sealed in this manner.

With a heat pack in which at least the earth-like mass is present in a granular form separately from the melting mass, the heat pack may be heated, after its removal from the packaging, while suspended in hot water vapor so that the pack itself is not merely heated, but also absorbs some water. The water or steam penetrates readily through the particles of the earth-like mass and this penetration is further facilitated by the holding fibers which have a capillary effect. The active ingredients cited hereinabove may also be introduced in a manner similar to water.

The two outer layers prevent the exit of the melting mass, especially when a thickener has been added and the melting mass is in a mixture with the earth-like mass, even when it has liquified.

The heated heat pack may be placed on the body, whereby the heat of crystallization of the melting mass is utilized for the thermal treatment of the part of the body to be treated. This effect and the associated treatment are known as such, as described hereinabove. However, by means of the configuration of the heat pack according to the present invention, it may be used in contrast to the known mud, paraffin and fango packs, by everyone without the need for special equipment.

An advantageous process for the preparation of a heat pack as described hereinabove comprises placing a layer of the earth-like mass and the melting mass between two flat outer layers and of joining the outer layers together by means of holding fibers distributed over the entire surface, through the inner layer. The two layers may have the configuration of a continuous web, whereby the preparation may be made continuous. If at least one of the outer layers is an actively needle bondable sheet, the two outer layers may be needle bonded together through the flat inner layer. For this purpose, a needle machine known from the manufacture of needle tufted carpets may advantageously be used. According to a further process step, the three web-like sheets joined together by means of holding fibers are divided into flat shapes according to their application and the heat pack formed in this manner packaged between two gas and water impermeable sheets, especially vacuum packed. If this division into flat shapes according to the application is effected with hot tools and the three layers simultaneously pressed together mechanically directly adjacent to the cutting line, the above-described heat packs are obtained with border strips thinner than the rest of the surface.

According to a particular embodiment, the holding fibers may be distributed simultaneously, spaced apart over the entire surface of the heat pack.

Further advantages and details of the invention shall become apparent from the following examples described with the aid of the drawing.

Figure 1:
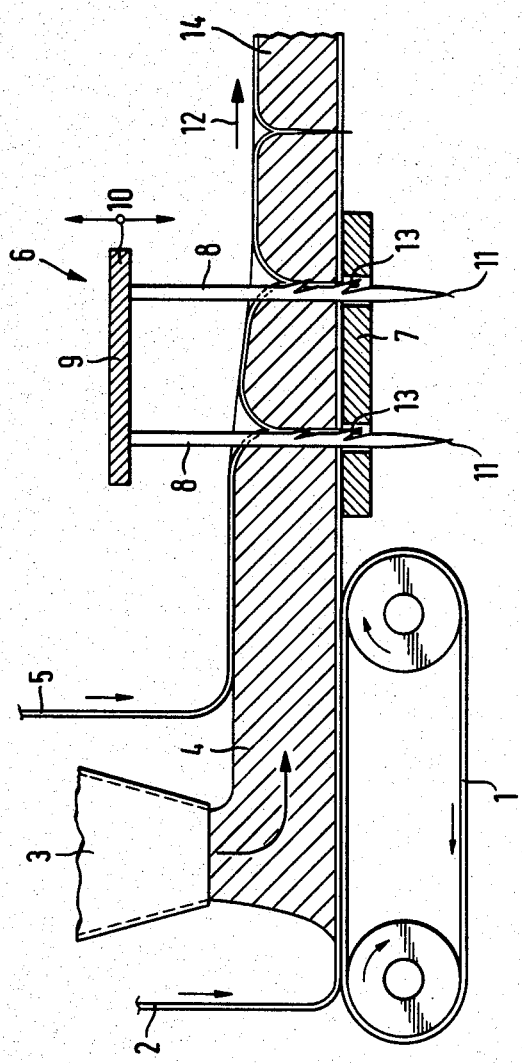
FIG. 1 shows part of a device for the preparation of a heat pack.

The step of the introduction of the holding fibers essential for the production of the heat pack is first described with respect to FIG. 1, this introduction being effected here by needle bonding.

According to FIG. 1, a first outer layer 2 is placed on a conveyor installation, here a conveyor belt 1, and the inner layer 4, consisting of an earth-like mass and a melting mass applied to layer 2 by means of a metering discharge device 3. Actively needle bondable fibers, here in the form of a fiber fleece 5, are placed on the layer 4 whereupon this three-layer system is transported to a needle machine 6.

Such needle machines are known from textile needle fleecing methods (see for example Krcma, "Non-woven Textiles" Pages 143-146). In such a needle machine 6, the system to be needle bonded, here the three-layer system, is guided over a base plate 7 provided with bore holes. A needle board 9 carrying the bonding needles 8 is arranged over the object to be needle bonded, this needle board moving constantly up and down (double arrow 10) over a distance such that the needle points 11 in the lowest position usually entirely penetrate the object to be bonded, while in their uppermost position, they are not in contact with the object to be bonded. In this uppermost position the object to be bonded (the three layer system), can be cyclingly advanced in the direction of travel (arrow 12), while during the needling process itself, it must be at rest. The bonding needles 8 carry on their shaft at least one—in this case two—barbs 13 whereby they seize the individual fibers or bundles of fibers and draw them into or through the object to be bonded. During the return of the needles 8, the fibers or bundles of fibers entrained are released from the barb 13 and remain in the passively needle bonded layer, here in the lower outside layer and the mixed layer 4. In needle bonding in the textile industry for the production of tufted carpets having a final thickness of, for example, 4-6 mm, the needle boards 9 are equipped with a plurality of needles arranged closely adjacent to each other and the needle board may be moved, for example, at a velocity of 700 strokes per minute. However, for the production of webs intended for heat packs and containing the earth-like mass and paraffin between the two outer layers 2 and 5, the number of needles 8 in the needle board 9 should be reduced and the number of strokes reduced for example to 200-500 strokes per minute.

It is further advisable to heat both the needles 8 and the base plate 7, together with the needle board 9, by means of hot air, for example, to the melting temperature of the melting mass, so that the needles may more easily penetrate the inner layer. It is further advantageous to heat the inner layer in the discharge device 3 to a temperature above the melting temperature of the melting mass, so that inner layer 4 itself remains viscous. If now the bonding needles 8 penetrate the three layer system and are then extracted from the outer layer 5 on top, the melting mass is released from the needles 8 at the latest at the outer layer 5.

As seen in FIG. 1, the thickness of the three layer system is reduced during the needling process, as first, the outer layer 5 containing the fibers is compressed by the needle process and second this outer layer 5, and depending on the configuration, the other outer layer 2 is drawn or pressured into the inner layer 4.

Figure 4:
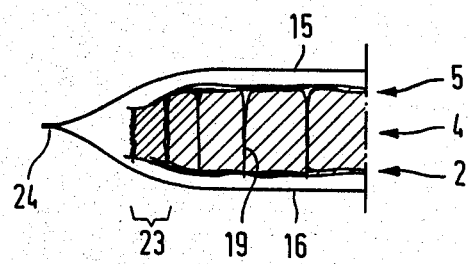
FIG. 4 shows a section through the border area of a packaged heat pack according to a third embodiment.

The web 14 exiting from the needle machine is then divided into individual packaging sizes depending on the intended application and packaged between two sheets 15 and 16, which shall be explained in more detail with regard to FIG. 4.

Figure 2:
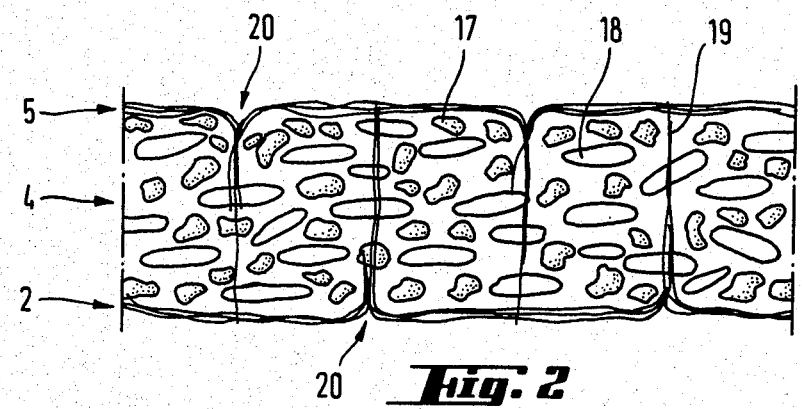
FIG. 2 shows a portion of a heat pack in cross section according to a first embodiment.

FIG. 2 shows a needle bonded heat pack, in which between the two outer layers 2 and 5, in this case each of which comprises a fiber fleece, is a layer 4 containing particles 17 of an earth-like mass and paraffin particles 18. FIG. 2 is an enlarged and schematized representation, whereby it may be seen that the two outer layers 2 and 5 are joined together by the holding fibers 19 extending through the mixed layer 4. The heat pack of FIG. 2 is needle bonded from the side of the two outer layers 2 and 5, as indicated by the "fiber funnels" 20 that are formed at the entry locations of the needles 8. Into these fiber funnels ends of fibers and parts of fiber not seized by the barbs 13 are also drawn in part. The holding fibers 19 penetrating the heat pack are distributed irregularly over the surface of the web and for this reason only very few of the holding fibers 19 may be seen in a section.

It is now apparent that between the particles 17 of the earth-like mass, comprising, for example, mud, fango, clay (healing earth) and the paraffin particles 18, certain interstices remain. These interstices are in actual practice smaller than those shown in the schematic representation, since as mentioned hereinabove, as the result of the needle bonding of the three layers the two outer layers are closer to each other than prior to needling. This follows on the one hand from the fact that very strong vibrations occur in the course of the process and on the other, that the holding fibers 19 are drawing the two outer layers 2 and 5 toward each other, so that they are applying a certain pressure to the mixed layer 4.

Figure 3:
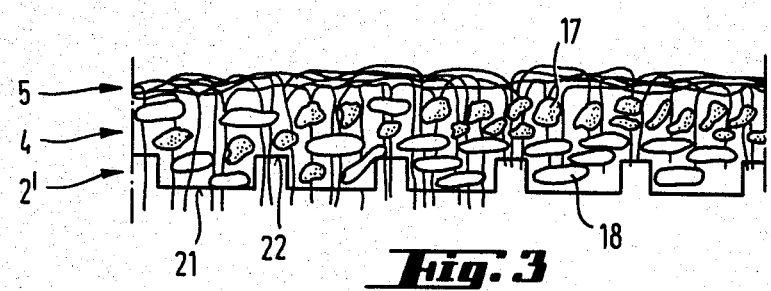
FIG. 3 shows a portion of a heat pack in cross section according to a second embodiment.

FIG. 3 shows a significantly different form of embodiment wherein one of the outer layers, i.e., the lower one in the drawing, comprises a so-called stepped sheet 2′.

This stepped sheet 2′ may be made of a synthetic plastic sheet, aluminum foil laminated to a plastic sheet, aluminum foil or a fiber composite, wherein the cuplets 21 may be formed for example by deep drawing, especially in the warm plastic state. The depressions of the cuplets 21 are filled with the mixture—or at least with a component of the mixture—with the total thickness of the mixed layer 4 being greater than the depth of the cuplets 21. In FIG. 3, the holding fibers are distributed completely uniformly over the surface of the heat pack. While in the left hand part of FIG. 3, the holding fibers 19 are penetrating through the entire heat pack, i.e., both through the bottom of the cuplets 21 and through the webs 22 connecting the cuplets, in the right hand part of FIG. 3, the holding fibers are not inserted as deeply, so that they penetrate the sheet 2′ only in the area of the webs 22, but are not held in the bottom of the cuplets 21. Configurations according to the right side of FIG. 3, in which the holding fibers penetrate only the webs, have a thicker outer layer 2′, than a pack corresponding to the left side of FIG. 3.

The left and right sides of FIG. 3 further differ in that in the left part the particles of the earth-like mass 17 and the paraffin particles 18 are distributed uniformly over the entire thickness of the pack, while in the area of the two right hand cuplets 21, the particles are present in separate layers with only paraffin particles 18 being present essentially adjacent to the sheet 2 and the particles 17 of the earth-like mass are essentially located next to the more permeable fiber fleece layer 5. If such a heat pack (as depicted on the right hand side of FIG. 3) is heated above the melting point of paraffin, so that the paraffin is liquified, it does not mix for the most part with the particles 17 of the earth-like mass, with the latter still remaining effective and capable of releasing any active ingredient (medicament) associated therewith.

FIG. 4 shows a heat pack, packaged between two sheets 15 and 16, in cross section. The heat pack is thinner at the borders 23 than at a distance from said borders, this effect being achieved during the cutting of the needle bonded web 14, which may be effected for example by means of a hot blade. The two outer layers 2 and 5 are thus mechanically pressed together directly adjacent to the cut lines, with the compression bonding the fibers with the melting mass. The borders 23 of the heat pack are thereby quasi-sealed.

This embodiment has an inner layer 4 of the heat pack in which the melting mass is completely intermixed with the earth-like mass, i.e., in the course of manufacture, a melt containing all of the components of the inner layer, was supplied. The inner layer 4 is homogeneous in itself and is penetrated only by the holding fibers 19.

According to another embodiment, not shown, a heat pack similar to those described hereinabove may be coated on its outer sides, where the other packs have fibers, with a thin layer of the earth-like mass and paraffin, so that the fibers of the outer layer are not visible on the finished pack.

The heat pack finished in this manner is inserted between the two sheets 15 and 16 forming an open bag, whereupon the bag is closed with the air contained therein being suctioned off. The presence of a vacuum in the bag formed from sheets 15 and 16 insures good storability over longer periods of time. Furthermore, the heat pack packaged in bags may be placed in a vessel with boiling water, for example, a cooking pot, whereby the heat pack itself remains dry and the paraffin is melted. If, on the other hand, the heat pack is to be used wet, small orifices may be produced in the packaging, for example with a fork, without having to place the heat pack totally unprotected into the water.

The composition and configuration of certain heat packs according to the invention will become apparent from the following examples.

EXAMPLE 1

To prepare the outer layer 5 permeable to liquid, a fleece of food resistant polypropylene fibers with a weight per unit area of 90 g, a titer of 6.7 dtex and a staple length of 90 mm was placed on a Bafatex support with a weight per unit area of 25 g/m$^2$. The fleece was pre-needle bonded to the passively needle bondable Bafatex support with a stitch density of 48 stitches per cm$^2$.

For the other outer layer 2, a fiber fleece of the same fibers was used; this fleece having a weight per unit area of 150 g/cm$^2$. The fleece again was needled onto a Bafatex support with a stitch density of 72 stitches per cm$^2$. This outer layer 2 was thus more dense than the outer layer 5.

For the mixed layer 4, a mixture of four parts by weight of dried mud and six parts by weight rasped paraffin was used. The mixture was applied with a weight per unit area of 12 kg/m$^2$ to the heavier outer layer 2 as described with regard to FIG. 1 hereinabove, whereupon the mixed layer was covered with the lighter outer layer 5 and the three layer system needle-bonded from both sides. The stitch density of each side amounted to 24 stitches per cm$^2$. The needle-bonded web 14 was then cut into individual heat packs with a surface area of 20×15 to 30×20 cm, whereby the two outer layers 2 and 5 were pressed together on their circumferential borders. A heat pack having two fibrous surfaces, one of which (5) being more permeable than the other (2) was obtained. The outer layer 5 is intended for contact with the body part to be treated. The heat packs were then placed between the two sheets forming bags, air in the bag suctioned off and the opening welded shut.

For application, the closed bag was placed in a cooking pot with boiling water and removed from the pot after 20 minutes. Following the tearing of the bag and removal of the heat pack, the latter was ready for application with its more permeable outer layer 5 applied to the body parts to be treated.

EXAMPLE 2

The two outer layers 2 and 5 were constructed exactly as the two outer layers 2 and 5 of Example 1 with the exception that here a mixture of polypropylene fibers was used wherein 85% of the fibers had a titer of 6.7 dtex and 15% a titer of 17 dtex.

As the mixed layer 4, a mixture of one part by weight of fango and one part by weight of rasped paraffin grains was used and the mixture placed with a weight per unit area of 10 kg/m$^2$ between the two outer layers 2 and 5, which in turn were needled and packaged as in Example 1. Prior to use, this parafango heat pack was taken from the bag and heated in a water bath with healing herbs for 10 minutes on a cooking plate so that steam bubbles are formed only on the bottom of the pot.

In the application of this heat pack to the human body, the herb ingredients essentially absorbed by the pack are effective for the human body.

EXAMPLE 3

The above-described lighter fiber layer was used as the more permeable outer layer 5. A stepped sheet was used as the denser outer layer 2, i.e., a plastic sheet coated with aluminum foil in which by deep drawing, circular depressions with a diameter of 10 mm and a depth of 5 mm were produced. The aluminum foil layer was on the side in which the cuplets formed the depressions. The plastic sheet consisted of polyethylene with a weight per unit area of 115 g/m$^2$. Onto the aluminum layer, especially into the depressions, a layer of finely rasped paraffin was placed with a weight per unit area of 7 kg/m$^2$. The paraffin layer was covered with a layer of dried mud with a weight of 3 kg/m$^2$ and the latter covered with a layer of fiber. The multiple layer system formed in this manner was needle bonded from the side of the fiber layer with a density of 72 stitches per cm$^2$, whereby the fibers penetrated not only the webs between the depressions but also the bottoms of the depressions.

This heat pack was again packaged in a foil bag as described in Example 1 and then heated in a hot, steaming water bath for 20 minutes. The bag was taken from the water bath, opened and held for approximately one minute over the steaming water, so that the steam would penetrate the fiber layer to the underlying mud layer. Using a parallel pattern, it was determined that even after the heating, there was no appreciable mixing of the paraffin with the mud.

The pack heated and moistened in this manner was again placed with the fiber layer on the body part to be treated. After 15 minutes, the body part was massaged through the heat pack. It was found that no essential displacement of the mud and paraffin mass located between the two outer layers takes place, while smaller mud particles, particularly as the result of the massage, penetrated the fiber layer. It was observed further that essentially no paraffin escaped through the plastic sheet at the locations perforated by the holding fibers, in spite of the massage, but that the paraffin completely sealed the perforated locations.

EXAMPLE 4

The method of Example 3 was repeated, with the holding fibers being needled in this time only deep enough to penetrate the webs between the depressions and stopping at a distance from the bottom of the depressions. To prevent the perforation of these bottoms by the points of the needles, special needles known in the textile industry were used. On these needles the distance of the last barb to the point is very short.

Even though in this embodiment, only part of the holding fibers connected the two outer sheets 2 and 5, it was possible to massage through this heat pack, since the holding fibers connecting the two outer layers in the area of the webs were sufficient to prevent the shifting of the mud particles and the paraffin in a direction parallel to the flat dimension of the layers.

EXAMPLE 5

To produce the two outer layers 2 and 5, a fleece each of food resistant polypropylene fibers with a unit weight of 120 g/m$^2$, a titer of 17 dtex and a staple length of 90 mm was placed on a wide mesh support made of crossed filaments with a unit weight of 42 g/m$^2$. This fleece was needle bonded to a passively needle bondable support with a stitch density of 27 stitches per cm$^2$, so that preneedled outer layers with a weight of 162 g/m$^2$ were obtained. For a homogeneous inner layer 4, 45% by weight paraffin, 42.5% by weight fango powder, 5% by weight talcum powder and 5.5% by weight of a thickener and means to prevent bleeding after the melting of the paraffin were mixed until a uniform mixture was obtained. This still liquid mixture was applied to the outer layer 2 by means of the discharge device with a layer thickness of 12 mm and a weight of 16 kg/m$^2$. The second outer layer 5 is placed onto this mixed layer. The three-layer system was needle-bonded from the side of both outer layers 2 and 5 with a stitch density on each side of 24 stitches per cm$^2$. During the needling, most of the mixture was still present in the molten state, surrounded only by the already solidified outer areas of the mixture and the two outer layers. The needles 8, the needle board 9 and the base plate 7 were heated with hot air approximately to the melting temperature of the melting mass so that the needles penetrating into the inner layer 4 were free from the molten mass upon their retraction from the fiber layer 5.

The needle bonded web 14 was then cut into individual heat packs with an area of 15×40 cm. A heat pack was obtained in this manner, both surfaces of which consisted of fibers. Individual heat packs were placed between sheets 15 and 16 forming the bags, the air in the bags suctioned off and the orifices welded shut.

For application, the sealed bag with the heat pack was placed in a pot of boiling water, which continued boiling and the bag was left therein for 15 minutes. The pack was then removed from the bag and after a few minutes of cooling the surface temperature of the pack measured. This was effected simply by placing the back of the hand on the pack to ascertain whether the skin will tolerate the heat. In this case, the pack had an approximate temperature of 52–54° C.

This strip-like pack was then placed onto the part of the body to be treated and in particular in the case of arms and legs, wound around these members. The pack was easily manipulated to contact the parts of the body involved over its entire surface. It was covered with a prepared piece of household foil and a wool blanket prior to letting the patient rest.

After the treatment, which lasted for 20 to 45 minutes, the pack was removed, flattened out and replaced in the bag, which is smoothed out to remove the air from it as much as possible, and the opening of the bag is then sealed.

Such a heat pack may be reused several times so that for a treatment of several weeks, it is sufficient to use a single heat pack. The packaged heat pack should be stored in a cool and dry location and prior to the next use, it is again placed in a boiling water bath in which it again becomes soft and elastic.

Even though the pack is 40 cm long, it is not necessary to use a water bath able to contain the entire rigid pack as it has been observed that the part of the pack initially immersed in the water bath softens rapidly enough for the rest of the pack to be able to slide into the water bath. The effect is similar to that observed in the cooking of spaghetti in which the part initially immersed in the water becomes soft enough for entry of the remainder.

The above-described examples make it apparent that a heat pack with a configuration according to the invention may be used in a more versatile manner than the known heat packs. For example, the mixed layer located behind the thinner outer layer 5 or the layer of the earth-like mass which is essentially dry, may be saturated with oils, sulfur, vegetable extracts or the like. This saturation may be effected immediately prior to the application, even by unskilled persons.

If, in certain healing processes, the heat is to act for a longer period of time on the part of the body to be treated, it is possible to fold the heat pack according to the invention so that different sections of the heat pack will be resting on each other. This results in a heat pack which has, for example, only one-half of the original surface area, but which is twice as thick. Heat packs may even be supplied in the folded state, whereby less space is required in the pot filled with water.

EXAMPLE 6

To a synthetic plastic sheet 2', in which by means of deep drawing circular depressions with a diameter of 20 mm and a depth of 10 mm were produced, a heated mixture of 75% by weight paraffin, 10% by weight ceresine wax, 10% by weight powdered sand, and 5% by weight talcum powder, was applied and covered with a layer of fibers. The plastic sheet used was a sheet of polyethylene with a unit weight of 115 g/m$^2$. The mixed layer 4 had a unit weight of 20 kg/m$^2$, while the unit weight of the fiber layer was 120 g/m$^2$; the latter was then needling to a wide mesh support. The three layers were then needle bonded so that the holding fibers penetrated the sheet only between the depressions and there were no penetrations by the needles in the depressions.

One such three-layer system was produced in webs with a width of 15 cm and a length of 10 m and the webs rolled up. The webs, representing a different type of heat pack, were rolled out in nurseries between rows of small plants so that the plastic sheet was on the ground and the fiber layer exposed to the sunlight. During the day, even a slight irradiation by the sun heated the heat pack, leading, depending on the intensity and duration of the irradiation, to the melting of the paraffin ceresine mixture. During the night, the pack slowly released its heat to the adjacent plants and the adjacent layer of the ground so that both the plants and the ground are kept at a temperature that was higher by a few ° C than that of the areas where no heat packs were used. In this application, the heat pack essentially serves as a heat reservoir, releasing the heat absorbed during the day at night. Also, the heat pack prevents the growth of undesirable weeds in the areas covered by the pack.

A heat pack according to the invention may further contain its own heating device, with for example, insulated heating wires being inserted between the two outer layers and adjacent to the earth-like mass and the melting mass. In this case, care must be taken during the needle bonding of such a three-layer system that the needles are inserted between the heating wires so that the insulation of the latter will not be damaged. On the other hand, due to the special configuration of the heat pack, it may be folded in the center, whereby two parts of the pack are resting on each other. The heating wires may then be arranged between the two parts of the pack. In view of the high heat storage capacity of the pack, the heat pack is able to release heat even long after the turning off of the electric current or the removal of the plug from the outlet.

I claim:

1. A heat pack comprising an inner layer located between two outer layers, the inner layer comprising an earth-like mass and a melting mass of wax and at least one of the outer layers comprising an actively needle bondable fiber fleece, said layers connected together by means of holding fibers.

2. A heat pack according to claim 1 wherein the three layers are needle bonded to each other.

3. A heat pack according to claim 1 wherein the earth-like mass is mud, fango, clay or medicinal earth and is present essentially in the dried form.

4. A heat pack according to claim 1 wherein the melting mass is a synthetic or natural hydrocarbon wax or mixtures thereof.

5. A heat pack according to claim 1 wherein the inner layer comprises 30–70% by weight of the earth-like mass and 70–30% by weight of the melting mass.

6. A heat pack according to claim 1 wherein the inner layer is present in a unit weight amount of 3–30 kg/m$^2$.

7. A heat pack according to claim 1 wherein the inner layer contains active ingredients, such as medicinal herbs, oils, sulfur or vegetable extracts.

8. A heat pack according to claim 1 wherein the said fiber fleece has a unit weight of 20–350 g/m$^2$.

9. A heat pack according to claim 1 wherein the other outer layer also comprises a fiber fleece and has a unit weight preferably of 100–180 g/m$^2$.

10. A heat pack according to claim 1 wherein the second outer layer comprises a foil.

11. A heat pack according to claim 10 wherein the foil is aluminum foil.

12. A heat pack according to claim 10, wherein the foil is a stepped foil.

13. A heat pack according to claim 1, wherein the holding fibers are provided with a surface density such that the earth-like mass and the melting mass are prevented from shifting.

14. A heat pack according to claim 1, wherein the holding fibers are drawing the two outer layers toward each other, so that they are applying pressure to the inner layer of the earth-like mass and the melting mass.

15. A heat pack according to claim 1, wherein the three-layer system has a lesser thickness at its circumferential borders than at a distance from said borders.

16. A heat pack according to claim 1, wherein the earth-like mass is present in granular form.

17. A heat pack according to claim 1, wherein the earth-like mass is present essentially in a dried form.

18. A heat pack according to claim 1, wherein the melting mass is present in the granular form.

19. A heat pack according to claim 1, wherein the melting mass is present in the form of a continuous layer penetrated by the holding fibers.

20. A heat pack according to claim 19, wherein the earth-like mass is embedded in the melting mass.

21. A heat pack according to claim 1, wherein the pack formed by the two outer layers and the inner layer of the earth-like mass and the melting mass are arranged between two gas and liquid tight foils and that said foils are joined together at their borders in a sealed manner.

22. A heat pack according to claim 21, wherein a vacuum is present between the two foils.

23. A process for the preparation of a heat pack according to claim 1, wherein a layer of an earth-like mass and a melting mass of wax is placed between two flat layers at least one of the outer layers comprising an actively needle bondable fleece, and that the two layers surrounding the inner layer are joined with each other by means of holding fibers through the inner layer.

24. A process according to claim 23, wherein the two outer layers are needle bonded to each other through the inner layer.

25. A process according to claim 23, wherein the three layers joined together by means of holding fibers are divided into flat pieces to form a pack and the pack obtained in this manner is packaged between two gas and water tight sheets.

26. A process according to claim 25, wherein the division into pieces according to application is effected by means of hot tools and the three layers are compressed simultaneously, directly adjacent to the cutting line, mechanically against each other.

27. A process according to claim 25, wherein the pack is vacuum packaged between the two sheets.

28. A heat pack according to claim 4, wherein the melting mass is paraffin.

29. A heat pack according to claim 5, wherein the mixing ratio is 1:1.

30. A heat pack according to claim 6, wherein the inner layer is present in a unit weight amount of 8–15kg/m$^2$.

31. A heat pack according to claim 8, wherein the fiber fleece has a unit weight ratio of 100–180 g/m$^2$.

32. A heat pack according to claim 10, wherein the foil has a unit weight of 50–200g/m$^2$.

33. A heat pack according to claim 1, wherein at least one outer layer is permeable to at least liquids and the proportion of the earth-like mass is higher in the vicinity of said outer layer than in the vicinity of the other outer layer.

* * * * *